United States Patent

Hausmann et al.

[11] Patent Number: 4,500,348
[45] Date of Patent: Feb. 19, 1985

[54] OIL-IN-WATER EMULSIONS, AND THEIR USE

[75] Inventors: Heinz Hausmann, Leichlingen; Heinz J. Niessen, Bergisch Gladbach; Otto Telle, Cologne; Hermann Neumaier, Leichlingen, all of Fed. Rep. of Germany

[73] Assignee: Bayer Aktiengesellschaft, Leverkusen, Fed. Rep. of Germany

[21] Appl. No.: 355,076

[22] Filed: Mar. 5, 1982

[30] Foreign Application Priority Data

Mar. 26, 1981 [DE] Fed. Rep. of Germany ....... 3111934

[51] Int. Cl.³ .............................. A01N 41/00
[52] U.S. Cl. ...................... 71/103; 71/122; 514/518
[58] Field of Search ............... 71/103, 122; 424/335

[56] References Cited

U.S. PATENT DOCUMENTS 2,552,187   5/1951   Kosmin ............................... 71/122

FOREIGN PATENT DOCUMENTS

| 55401 | 7/1982 | European Pat. Off. ............. | 71/122 |
| 824949 | 1/1952 | Fed. Rep. of Germany ........ | 71/103 |
| 1121814 | 1/1962 | Fed. Rep. of Germany ........ | 71/103 |
| 2041480 | 2/1972 | Fed. Rep. of Germany ........ | 71/103 |
| 2452250 | 10/1980 | France ................................. | 71/122 |
| 44-17400 | 7/1969 | Japan .................................. | 71/122 |

Primary Examiner—Paul J. Killos
Attorney, Agent, or Firm—Sprung Horn Kramer & Woods

[57] ABSTRACT

Novel oil-in-water emulsions, which contain (a) 0.1 to 80% by weight of at least one sparingly water-soluble active compound (as herein defined) selected from agrochemical active compounds, active compounds for combating pests in the domestic field and hygiene field and/or pharmacologically active compounds, (b) 1 to 20% by weight of at least one alkylaryl polyglycol ether of the general formula

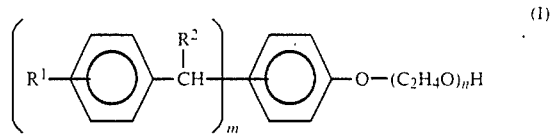

wherein
$R^1$ represents a hydrogen atom or an alkyl group having 1 to 16 carbon atoms,
$R^3$ represents a hydrogen atom or a methyl group,
m is 1, 2 or 3, and
n is an integer from 10 to 50,
if appropriate in a mixture with an alkylarylsulphonic acid salt of the general formula

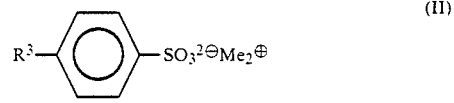

wherein
$R^3$ represents an alkyl group having 8 to 35 carbon atoms and
$Me^\oplus$ represents an alkali metal cation, an equivalent of an alkaline earth metal cation or a cation of the general formula

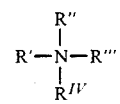

wherein
R', R'', R''' and $R^{IV}$ independently of one another represent a hydrogen atom, an alkyl group having 1 to 4 carbon atoms or a hydroxyalkyl group having 1 to 4 carbon atoms,
(c) water,
(d) if necessary, 1 to 30% by weight of at least one poorly water-miscible organic solvent and/or a solubilizer, and
(e) if appropriate 0.05 to 15% by weight of one or more additives,
the sum of the components being 100% by weight in each case,
a process for the preparation of these emulsions and their use in the field appropriate to the active compound.

13 Claims, No Drawings

OIL-IN-WATER EMULSIONS, AND THEIR USE

This invention relates to certain new oil-in-water emulsions of agrochemical active compounds, active compounds for combating pests in the domestic field and hygiene field and/or pharmacologically active compounds. In an additional aspect the invention relates to a process for the preparation of such oil-in-water emulsions. In still further aspect, the invention relates to the use of such oil-in-water emulsions.

Oil-in-water emulsions containing in each case, in addition to various sparingly water-soluble agrochemical active compounds, either a surface-active substance and a thickener, or a relatively large quantity of surface-active substances, are known (see German Patent Application No. 3,009,944, German Patent Application No. 3,011,611 and Japanese Patent Application No. 122,628-77). The need to add thickener or larger quantities of tensides is associated with additional costs and thus represents a serious disadvantage of the known oil-in-water emulsions. In addition, the previously described preparation of emulsions of this type is not generally applicable. In particular, according to this method, essentially only those sparingly water-soluble active compounds which are liquid at room temperature or at least have a very low melting point can be emulsified. The fact that the known oil-in-water emulsions are frequently insufficiently stable to frost and that, in many cases, a forced emulsification with the aid of homogenisers is necessary are further disadvantages.

The present invention now provides oil-in-water emulsions, which contain (a) 0.1 to 80% by weight of at least one sparingly water-soluble active compound (as herein defined) selected from agrochemical active compounds, active compounds for combating pests in the domestic field and hygiene field and/or pharmacologically active compounds, (b) 1 to 20% by weight of at least one alkylaryl polyglycol ether of the general formula

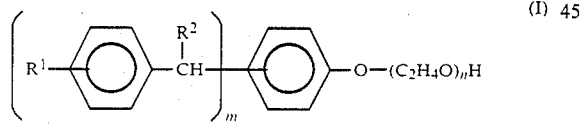

wherein
$R^1$ represents a hydrogen atom or an alkyl group having 1 to 16 carbon atoms,
$R^2$ represents a hydrogen atom or a methyl group,
m is 1, 2 or 3 and
n is an integer from 10 to 50,
if appropriate in a mixture with an alkylarylsulphonic acid salt of the general formula

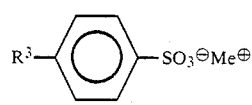

wherein
$R^3$ represents an alkyl group having 8 to 35 carbon atoms and $Me^\oplus$ represents an alkali metal cation, an equivalent of an alkaline earth metal cation or a cation of the general formula

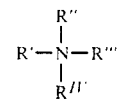

wherein
$R'$, $R''$, $R'''$ and $R^{IV}$ independently of one another represent a hydrogen atom, an alkyl group having 1 to 4 carbon atoms or a hydroxyalkyl group having 1 to 4 carbon atoms, (c) water,
(d) if necessary, 1 to 30% by weight of at least one poorly water-miscible organic solvent and/or a solubiliser, and
(e) if appropriate 0.05 to 15% by weight of one or more additives,
the sum of the components being 100% by weight in each case.

The present invention further provides a process for the production of an oil-in-water emulsion according to the invention, in which a homogeneous mixture of at least one sparingly water-soluble active compound selected from agrochemical active compounds, active compounds for combating pests in the domestic field and hygiene field and/or one pharmacologically active compounds; at least one alkylaryl polyglycol ether of the general formula

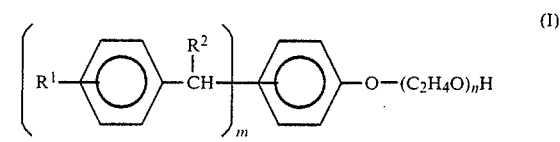

wherein
$R^1$, $R^2$, m and n have the meaning given above, if appropriate in a mixture with alkylarylsulphonic acid salts of the general formula

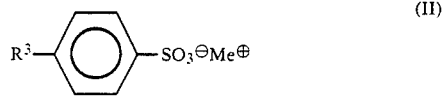

wherein
$R^3$ and $Me^\ominus$ have the meaning given above; if necessary at least one poorly water-miscible organic solvent and/or a solubiliser; and if appropriate one or more additives;
is added, whilst stirring, to water which contains one or more additives, if appropriate, the quantity of components in the mixture and of any additives and the quantity of mixture being such that the resulting emulsion comprises the percentages by weight of components given above.

It has been found that the oil-in-water emulsions according to the invention, depending on the active compounds contained, are appropriate formulations for use for various purposes in agriculture and horticulture, in the domestic field and hygiene field or in the medical field.

It is to be regarded as extremely surprising that the oil-in-water emulsions according to the invention are stable, since it was to be expected on the basis of the known state of the art that emulsions of this type, which contain no thickeners and also only a small proportion of tensides, could not be kept for relatively long periods. Thus, it is evident from German Patent Application No. 3,009,944 and German Patent Application No. 3,011,611 that the oil-in-water emulsions described in these patent applications necessarily contain a thickener as a stabiliser. The emulsions disclosed in Japanese Patent Application No. 122,628-77 have a very high proportion of tensides in proportion to the quantity of active compound. It was therefore not possible to foresee the outstanding stability of the oil-in-water emulsions according to the invention.

The oil-in-water emulsions according to the invention are distinguished by a number of advantages. Thus, an expensive addition of thickeners of large quantities of emulsifiers is unnecessary in their preparation. Furthermore, these emulsions contain either no organic solvents or only an extremely small quantity of organic solvents. They are therefore not combustible, free, or at least almost free, from odour nuisances through organic solvents, and have a lower toxicity or phytotoxicity than corresponding formulations which contain organic solvents in the otherwise customary concentrations. In addition, the oil-in-water emulsions according to the invention are stable under the conditions prevailing in practice. On long-term storage, these emulsions remain stabil at temperatures of 50° C. as well as at low temperatures. Finally, the oil-in-water emulsions can be prepared in a simple manner. A forced emulsification with the aid of homogenisers is unnecessary. In addition, a very considerable advantage is the fact that sparingly water-soluble active compounds which are solid or liquid at room temperature can be equally well emulsified.

The oil-in-water emulsions according to the invention contain at least one sparingly water-soluble active compound selected from agrochemical active compounds, active compounds for combating pests in the domestic field and hygiene field and/or pharmacologically active compounds. The active compound or compounds is, or are, present in the liquid state in the oil phase.

Those substances which are liquid at room temperature as well as those which are solid at room temperature are suitable active compounds. The precondition for liquid active compounds is merely that they are sparingly soluble in water. The term "sparingly water-soluble" used herein is to be understood here as meaning substances with a maximum solubility of 0.5% by weight in water at 20° C., and, where the active compounds is solid it must, in addition, be sufficiently soluble in a poorly water-miscible organic solvent and/or in a solubiliser to be taken up in the oil phase.

Agrochemical compounds are to be understood in the present case as meaning any of the sparingly water-soluble active compounds which can customarily be used in plant protection. These include, for example, insecticides, acaricides, nematicides, fungicides, herbicides, growth regulators and fertilisers.

The following may be individually mentioned as examples of active compounds of this type:
O,O-diethyl O-(4-nitro-phenyl)thiono-phosphate, O,O-dimethyl O(4-nitro-phenyl)thiono-phosphate, O-(ethyl O-(4-methylthio-phenyl)S-propyl dithiophosphate, (O,O-diethylthionophosphoryl)-α-oximino-phenylacetic acid nitrile, 2-isopropoxy-phenyl N-methyl carbamate, 3-methylthio-4-amino-6-tert.-butyl-1,2,4-triazin-5-one, 3-methylthio-4-isobutylideneamino-6-tert.-butyl-1,2,4-triazin-5-one, 2-chloro-4-ethylamino-6-isopropylamino-1,3,5-triazine, 2,3-dihydro-2,2-dimethyl-7-benzofuranyl-methyl carbamate, 3,5-dimethyl-4-methylthio-phenyl N-methyl carbamate, O,O-diethyl O-(3-chloro-4-methyl-7-coumarinyl)thiophosphate, γ-hexachlorocyclohexane, 6,7,8,9,10,10-hexachloro-1,5,5A,6,9,9A-hexahydro-6,9-methane-2,4,3-benzodioxathiepin-3-oxide, 1,4,5,6,7,8,8-heptachloro-4,7-endo-methylene-3A,4,7,7A-tetrahydroindene, 2-(2-furyl)-benzimidazole, 5-amino-1-bis(dimethylamido)-phosphoryl-3-phenyl-1,2,4-triazole, 4-hydroxy-3-(1,2,3,4-tetrahydro-1-naphthyl)-coumarin, S-[1,2-bis-(ethoxycarbonyl)-ethyl] O,O-dimethyl-dithiophosphate, O,O-dimethyl O-(4-methylmercapto-3-methyl-phenyl)thionophosphate, O-ethyl-O-(2-isopropyloxycarbonyl-phenyl)-N-isopropyl-thionophosphoric acid ester amide, 1-(4-chlorophenoxy)-3,3-dimethyl-1-(1,2,4-triazol-1-yl)-2-butanone and (S)-α-cyano-3-phenoxybenzyl-(1R)-cis-3-(2,2-dibromovinyl)-2,2-dimethylcyclopropanecarboxylate, 2,2-dimethyl-3-(β,β-dichlorovinyl)-cyclopropane-carboxylic acid α-cyano-3-phenoxy-4-fluoro-benzylester.

Active compounds for combating pests in the domestic field and hygiene field are to be understood in the present case as meaning any of the customary sparingly water-soluble pesticidally active compounds.

The following may be individually mentioned as examples of active compounds of this type:
2-isopropoxy-phenyl N-methyl carbamate, O,O-diethyl O-(4-nitro-phenyl)thionophosphate, O,O-dimethyl O-(4-nitrophenyl)thionophosphate, S-[1,2-bis-(ethoxycarbonyl)-ethyl] O,O-dimethyl dithiophosphate, O,O-dimethyl O-(3-methyl-4-nitro-phenyl)thionophosphate, O,O-dimethyl O-(4-methylmercapto-3-methyl-phenyl)thionophosphate, γ-hexachlorocyclohexane and (cyclohex-1-ene-1,2-dicarboximidomethyl)-2,2-dimethyl-3-(2-methylpropenyl)-cyclopropanecarboxylate.

Pharmacologically active compounds are to be understood in the present case as meaning sparingly water-soluble compounds which can preferably be employed in the field of veterinary medicine.

The following may be mentioned as an example of active compounds of this type:
α-cyano-3-phenoxy-4-fluoro-benzyl 2,2-dimethyl-3-[β-(p-chloro-phenyl)-β-chlorovinyl]-cyclopropanecarboxylate.

Formula (I) gives a general definition of the alkylaryl polyglycol ethers which are contained as emulsifiers in the oil-in-water emulsions according to the invention.

Preferred ethers of formula (I) are those in which R¹ represents a hydrogen atom or a straight-chain or branched alkyl group having 1 to 12 carbon atoms, R² represents a hydrogen atom or a methyl group, m is 2 or 3, and n is an integer from 12 to 40.

In formula (I) the integer for n represents an average value.

The following may be individually mentioned as examples of alkylaryl polyglycol ethers of the formula (I):
bis-[(p-methyl)-styryl]-phenol polyethylene oxide having an average of 27 ethylene oxide units per molecule, bis-[(p-dodecyl)-styryl]-phenol polyethylene oxide having an average of 27 ethylene oxide units per molecule, bis-[(p-methyl)-benzyl]-phenol polyethylene oxide having an average of 27 ethylene oxide units per molecule and tris-[(p-methyl)-styryl]-phenol polyethylene oxide having an average of 17 ethylene oxide units per molecule.

The emulsifiers of this type which are used in practice are generally mixtures of several compounds of the formula (I). In particular, these emulsifiers are mixtures of compounds of the formula (I), which differ in the degree of substitution at the phenyl ring bonded to the ethylene oxide unit. Such mixtures may be represented by an average formula in which m is a non-integral number as an average value. Substances with the following average formulae may be mentioned as examples:

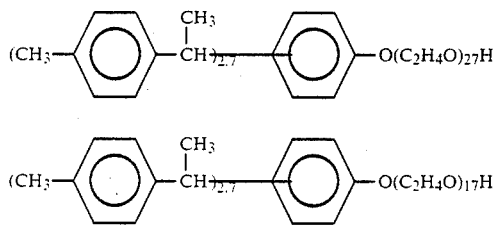

The alkylaryl polyglycol ethers of the formula (I) are known.

Formula (II) gives a general definition of the alkylaryl-sulphonic acid salts which are contained, if appropriate, in the oil-in-water emulsions according to the invention.

Preferred salts of formula (II) are those in which

R represents a straight-chain or branched alkyl group having 9 to 30 carbon atoms, and $Me^\oplus$ represents a sodium cation, an equivalent of a calcium cation or a cation of the general formula

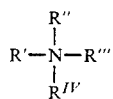

wherein $R'$, $R''$, $R'''$ and $R^{IV}$ independently of one another represent a hydrogen atom, an alkyl group having 1 or 2 carbon atoms or a hydroxyalkyl group having 1 or 2 carbon atoms.

The following may be individually mentioned as examples of alkylaryl-sulphonic acid salts of the formula (II):

sodium 4-(n-nonyl)-phenyl-sulphonate, calcium 4-(n-dodecyl)-phenyl-sulphonate, sodium 4-(tetrapropylene)-phenyl-sulphonate, calcium 4-(n-nonyl)-phenyl-sulphonate, ammonium 4-(i-dodecyl)-phenyl-sulphonate and 2-hydroxyethyl-ammonium 4-(n-dodecyl)-phenyl-sulphonate, The alkylaryl-sulphonic acid salts of the formula (II) are known. They are generally employed as 50 to 75% strength by weight solutions in organic solvents, for example n- or i-butanol, but can, in principle, also be used without a solvent.

Any of the customary poorly water-miscible organic solvents are suitable as organic solvents which can be contained, if appropriate, in the oil-in-water emulsions according to the invention.

The following may be preferably mentioned: aromatic hydrocarbons, such as xylene, toluene and dimethylnaphthalene, chlorinated aromatic hydrocarbons, such as benzine and petroleum ether, and furthermore halogenated aliphatic hydrocarbons, such as methylene chloride and chloroform, as well as cycloaliphatic hydrocarbons, such as cyclohexane, and furthermore alcohols and ketones, such as n-butanol, n-hexanol, iso-hexanol, n-octanol, cyclohexanol, benzylalcohol, di-n-butyl ketone and isophorone, and also ethers and esters, such as glycolmonomethylether and glycolmonomethylether acetate.

Any of the customary solubilisers are suitable as solubilisers which can be contained in the oil-in-water emulsions according to the invention. Alkylphenols or cresols which are condensed with 1 to 8 mol of ethylene oxide per mol are preferably usable. p-Cresol which is condensed with 1 to 8 mol of ethylene oxide per mol may specially be mentioned in this context.

Suitable additives which can be contained, if appropriate, in the oil-in-water emulsions according to the invention are preservatives, dyestuffs, frost stabilisers and synergists.

2-Hydroxy-biphenyl and sorbic acid may be mentioned as examples of preservatives. Azo dyestuffs and phthalocyanine dyestuffs may be quoted as examples of dyestuffs. Urea, sugar and salts, such as ammonium sulphate and sodium oleate, may be mentioned as examples of frost stabilisers, 3,4-Methylenedioxy-6-propyl-benzyl-n-butyl-diethyleneglycolether may be mentioned as an example of a synergist.

The percentage proportions of the components contained in the oil-in-water emulsions according to the invention can be varied within the specified ranges. The proportion of active compound or active compounds of component (a) is between 0.1 and 80% by weight, preferably between 5 and 80% by weight. The proportion of alkylaryl polyglycol ethers of the formula (I) of component (b), if appropriate in a mixture with alkylaryl-sulphonic acid salts of the formula (II), is 1 to 20% by weight, preferably 3 to 15% by weight. Poorly water-miscible organic solvents and/or solubilisers of component (d) are contained in proportions of from 1 to 30% by weight, preferably of from 5 to 20% by weight. Additives of component (e) are contained in proportions of from 0.05 to 15% by weight, preferably of from 0.1 to 10% by weight. The percentage proportion of water in the oil-in-water emulsions according to the invention is calculated, in each case, as the difference between 100% by weight and the sum of the percentage proportions of the remaining components.

In the oil-in-water emulsions according to the invention, the ratio of active compound(s), if appropriate in a mixture with organic solvents and/or solubilisers, on the one hand, to the alkylaryl polyglycol ether, if appropriate in a mixture with the alkylaryl-sulphonic acid salt, on the other hand, can be varied within a certain range. In general, 1 to 8 parts by weight, preferably 2 to 6 parts by weight, of active compound(s), if appropriate in a mixture with organic solvents and/or solubilisers, are employed per part of emulsifier (or emulsifier mixture).

Preferred components to be used in the preparation of the oil-in-water emulsions according to the invention are any of those components which have already been mentioned as preferred in connection with the description of the oil-in-water emulsions according to the invention.

If an active compound which is present in the liquid state at temperatures up to 40° C. is used in the process according to the invention, the addition of a poorly water-miscible organic solvent and/or of a solubiliser is generally unnecessary.

If an active compound which is present in the solid state at temperatures up to 40° C. is used in the process according to the invention, it is necessary to dissolve the particular active compound, before emulsification, in a poorly water-miscible organic solvent and/or solubiliser. The quantity of organic solvent and/or solubiliser is thereby proportioned so that it is just sufficient for dissolving the solid substance.

The temperature can be varied within a wide range in the process according to the invention. In general, the process is carried out at a temperature between 10° C. and 80° C., preferably between 20° C. and 60° C.

The process according to the invention is generally carried out in such a manner that a homogeneous solution of one or more active compounds, the alkylaryl polyglycol ether, if appropriate the alkylaryl-sulphonic acid salt, if appropriate the poorly water-miscible organic solvent and/or the solubiliser, and if appropriate additives, is first prepared, and this mixture is then added, whilst stirring, to water which contains additives if appropriate. In this process, the quantities of the components are chosen so that the components are present in the particular desired concentration in the resulting oil-in-water emulsion. The sequence in which the components are added to the organic phase is variable. The addition of the organic phase to the aqueous phase is advantageously effected slowly, whilst uniformly stirring with customary stirring devices. In this process, a fine-particled microemulsion is formed, in which the droplets have a diameter of between $0.05\mu$ and $1\mu$. When the organic phase is added rapidly to the aqueous phase the spectrum of droplet sizes is wider and is shifted toward particles with a larger diameter. An after-treatment, with homogenisers, of the resulting oil-in-water emulsion is not necessary, but can be carried out if desired.

The oil-in-water emulsions according to the invention can be applied either in the prepared form or after previous dilution. The use quantity depends on the concentration of the oil-in-water emulsion and on the particular indication.

The oil-in-water emulsions according to the invention are used according to customary methods, that is to say, for example, by squirting, spraying or pouring.

The preparation of the oil-in-water emulsions according to the invention is illustrated by the Examples which follow.

PREPARATIVE EXAMPLES

EXAMPLE 1

10.0 g of an emulsifier mixture, which consisted of equal parts of the components which can be described by the following average formulae:

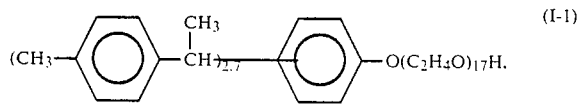

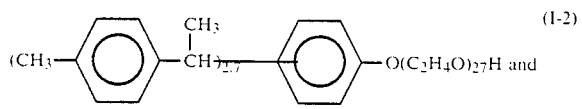

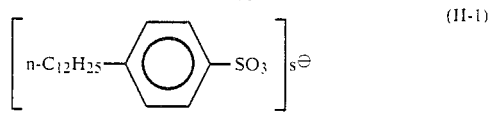

(70% strength by weight solution in n-butanol), were added to 25.0 g of the insecticidal active compound O,O-dimethyl-O-(4-methylmercapto-3-methyl-phenyl)thionophosphate, whilst stirring, at a temperature between 20° C. and 40° C. The homogeneous solution thereby formed was added, during the course of 2 minutes, to a solution of 0.2 g of 2-hydroxy-biphenyl in 64.8 g of distilled water, which solution was stirred with a blade stirrer at a speed of 2,000 revolutions per minute. After the addition had ended, the mixture was further stirred for 5 minutes. A viscous colloidal emulsion of reddish appearance was formed, which exhibited no physical or chemical changes when stored for twenty weeks at a temperature below 35° C.

EXAMPLE 2

12 g of an emulsifier mixture, which consisted of 80% by weight of the alkylaryl polyglycol ether of the average formula (I-1), as given in Example 1, and of 20% by weight of calcium 4-(n-dodecyl)-phenyl-sulphonate of the formula (II-1), as given in Example 1, (in the form of a 70% strength by weight solution in n-butanol), was added to 50 g of O,O-dimethyl O-(4-methylmercapto-3-methyl-phenyl)thionophosphate, whilst stirring, at a temperature between 20° and 40° C. The homogeneous solution thereby formed was added, during the course of 3 minutes, to a solution of 0.2 g of 2-hydroxy-biphenyl in 37.8 g of distilled water, which solution was stirred with a blade stirrer at a speed of 2,000 revolutions per minute. A highly viscous colloidal emulsion of reddish appearance was formed, which exhibited no physical or chemical changes when stored for twenty weeks at a temperature below 35° C.

EXAMPLE 3

20.0 g of a solubiliser, which had been prepared by condensing 1.5-2.0 mol of ethylene oxide with 1.0 mol of p-cresol, were added to 25.0 g of O-ethyl O-(3-methyl-4-methylthiophenyl) N-isopropyl phosphoramidate. The mixture was stirred at room temperature until the solids had completely dissolved, and 2.0 g of an emulsifier mixture, consisting of equal parts of compounds of the average formulae (I-1), (I-2) and (II-1), as given in Example 1, and 10.0 g of an emulsifier of the average formula (I-1) were then added successively. The homogeneous solution thereby formed was added, during the couse of 2 minutes, to a solution of 0.2 g of 2-hydroxy-biphenyl in 42.8 g of distilled water, which solution was stirred with a blade stirrer at a speed of 2,000 revolutions per minute. After the addition had ended, the mixture was further stirred for 6 minutes. A slightly yellowish viscous colloidal emulsion was formed, which exhibited no physical or chemical change, even after weeks, when stored at a temperature below 35° C.

EXAMPLE 4

An organic phase composed of 25.0 g of O-ethyl S-propyl-O-(4-methylmercapto-phenyl)thionophosphate and 10.0 g of an emulsifier of the average formula (I-1), as given in Example 1, was stirred into an aqueous phase composed of 0.2 g of 2-hydroxy-biphenyl and 64.8 g of distilled water, according to the method given in Example 1. A slightly viscous white emulsion was formed, which exhibited no physical or chemical change when stored for twenty weeks at a temperature of up to 40° C.

EXAMPLE 5

An organic phase composed of 1 g of 2-isopropoxyphenyl N-methyl carbamate, 0.2 g of (cyclohex-1-ene-1,2-dicarboximidomethyl)-2,2-dimethyl-3-(2p-methyl-propenyl)-cyclopropanecarboxylate, 1.0 g of 3,4-methylenedioxy-6-propylbenzyl-N-butyldiethylene glycol ether, 5.0 g of n-hexanol, 5.0 g of xylene, 6.0 g of kerosene and 5.0 g of an emulsifier mixture consisting of 80% by weight of a compound of the average formula (I-1), as given in Example 1, and 20% by weight of a compound of the formula (II-1), as given in Example 1, was stirred into 76.8 g of distilled water, according to the method given in Example 3. A yellowish-white microemulsion was formed, which exhibited no chemical or physical change after storage for eight weeks at 54° C.

EXAMPLE 6

An organic phase composed of 25.0 g of the insecticidal active compound, O,O-dimethyl O-(4-methylmercapto-3-methyl-phenyl)-thionophosphate and 10.0 g of the emulsifier given in Example 1, was stirred into 65.0 g of distilled water, according to the method given in Example 1. A viscous colloidal emulsion of reddish appearance was formed, which exhibited no physical or chemical changes when stored for 20 weeks at a temperature below 35° C.

EXAMPLE 7

An organic phase composed of 25.0 g of the insecticidal active compound O,O-dimethyl O-(4-methylmercapto-3-methyl-phenyl)-thionophosphate and 7.0 g of the emulsifier given in Example 1 and 0.7 g of benzylalcohol was stirred into 67.3 g of distilled water, according to the method given in Example 1. A viscous colloidal emulsion of reddish appearance was formed, which exhibited no physical or chemical changes when stored for 20 weeks at a temperature below 35° C.

EXAMPLE 8

An organic phase composed of 5.0 g of 2,2-dimethyl-3-($\beta,\beta$-dichlorovinyl)-cyclopropane-carboxylic acid $\alpha$-cyano-3-phenoxy-4-fluoro-benzylester, 10.0 g of xylene and 8.0 g of an emulsifier, which consisted of 48% by weight of the alkylaryl polyglycol ether of the average formula (I-2), as given in Example 1, 32% by weight of calcium 4-(n-do-decyl)-phenyl-sulphonate of the formula (II-1), as given in Example 1, 16% by weight of n-butanol and 4% by weight of xylene, was stirred into 77.0 g of distilled water, according to the method given in Example 3. A microemulsion was formed, which exhibited no chemical or physical change when stored for 20 weeks at a temperature below 35° C.

EXAMPLE 9

An organic phase composed of 5.0 g of 2,2-dimethyl-3-($\beta,\beta$-dichlorovinyl)-cyclopropane-carboxylic acid $\alpha$-cyano-3-phenoxy-4-fluoro-benzylester, 10.0 g of xylene, 2.0 g of n-butanol and 5.0 g of an emulsifier, which consisted of 48% by weight of the alkylaryl polyglycol ether of the average formula (I-2), as given in Example 1, 32% by weight of calcium 4-(n-dodecyl)-phenyl-sulphonate of the formula (II-1), as given in Example 1, 16% by weight of n-butanol and 4% by weight of xylene, was stirred into 78.0 g of distilled water, according to the method given in Example 3. A microemulsion was formed, which exhibited no chemical or physical change when stored for 20 weeks at a temperature below 35° C.

It will be understood that the specification and examples are illustrative but not limitative of the present invention and that other embodiments within the spirit and scope of the invention will suggest themselves to those skilled in the art.

What is claimed is:

1. Oil-in-water emulsion comprising
   (a) 5 to 80% by weight of at least one agrochemically active compound having a maximum solubility of 0.5% by weight in water at 20° C.,
   (b) 3 to 15% by weight of at least one alkylaryl polyglycol ether of the formula

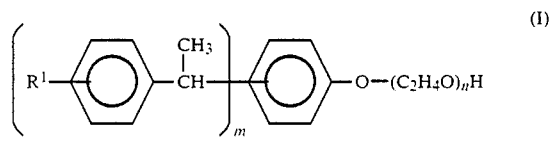

wherein
R$^1$ represents a hydrogen atom or an alkyl group having 1 to 12 carbon atoms,
m is 2 or 3 and
n is an integer from 12 to 40,
in admixture with an alkylarylsulphonic acid salt of the general formula

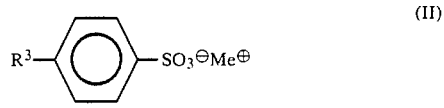

wherein
R$^3$ represents an alkylgroup having 9 to 30 carbon atoms and
M$^\oplus$ represents a sodium cation or an equivalent of a calcium cation, and
   (c) water.

2. Emulsion as claimed in claim 1 wherein the active component (a) is O,O-dimethyl-O-(4-methylmercapto-3-methyl-phenyl)-thionophosphate.

3. Emulsion as claimed in claim 1, in which the active component (a) is an insecticide, acaricide, nematicide, fungicide, herbicide, growth regulator or a fertiliser.

4. Emulsion as claimed in claim 1, in which the active component (a) is O,O-dimethyl-O-(4-methylmercapto-3-methylphenyl)-thionophosphate.

5. Emulsion as claimed in claim 1, in which the active component (a) is O-ethyl-O-(3-methyl-4-methylthiophenyl)N-isopropyl phosphoramidate.

6. Emulsion as claimed in claim 1, in which the active component (a) is O-ethyl-S-propyl-O-(4-methylmercapto-phenyl)-thionophosphate.

7. Emulsion as claimed in claim 1, in which the active component (a) is (cyclohex-1-ene-1,2-dicarboximidomethyl)-2,2-dimethyl-3-(2-methylpropenyl)-cyclopropanecarboxylate.

8. Emulsion as claimed in claim 1, in which the active component (a) is 2,2-dimethyl-3-($\beta,\beta$-dichlorovinyl)- cyclopropane-carboxylic acid α-cyano-3-phenoxy-4-fluoro-benzylester.

9. Emulsion as claimed in claim 1, in which the salt of the fomrula (II) is 4-(n-dodecyl)-phenyl-sulphonate.

10. A method of applying a sparingly water soluble agrochemically active compound to a plant or locus in which a plant is to be grown, which comprises applying to said plant or locus an agrochemically effective amount of an oil-in water emulsion comprising
(a) 5 to 80% by weight of at least one agrochemically active compound having a maximum solubility of 0.5% by weight in water at 20° C.
(b) 3 to 15% by weight of at least one alkylaryl polyglycol ether of the general formula

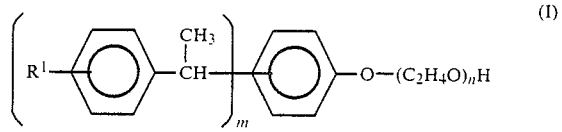

wherein
R¹ represents a hydrogen atom or an alkyl group having 1 to 12 carbon atoms,
m is 2 or 3 and
n is an integer from 12 to 40,
in admixture with an alkylarylsulphonic acid salt of the formula

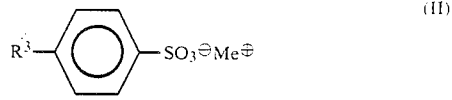

wherein
R³ represents an alkylgroup having 9 to 30 carbon atoms and
M⊕ represents a sodium cation or an equivalent of a calcium cation, and
(c) water.

11. Emulsion as claimed in claim 1, further containing 5 to 20% by weight of at least one poorly water-miscible organic solvent and/or solubilizer.

12. A method as claimed in claim 10, wherein the emulsion further contains 5 to 20% by weight of at least one poorly water-miscible organic solvent and/or solubilizer.

13. Emulsion as claimed in claim 11, in which the solubiliser is p-cresol which is condensed with 1 to 8 mol of ethylene oxide per mol.

* * * * *